United States Patent [19]

Hashimoto et al.

[11] Patent Number: 4,698,209
[45] Date of Patent: Oct. 6, 1987

[54] DEVICE FOR SENSING AN OXYGEN CONCENTRATION IN GASEOUS BODY WITH A SOURCE OF PUMP CURRENT FOR AN OXYGEN PUMP ELEMENT

[75] Inventors: Kenshiro Hashimoto, Tokyo; Yasushi Okada, Fujimi, both of Japan

[73] Assignee: Honda Giken Kogyo Kabushiki Kaisha, Tokyo, Japan

[21] Appl. No.: 875,455

[22] Filed: Jun. 18, 1986

[30] Foreign Application Priority Data

Jun. 21, 1985 [JP] Japan .................. 60-136479

[51] Int. Cl.$^4$ .............. G01N 27/00; G01N 27/26; G01N 30/96
[52] U.S. Cl. ......................... 422/88; 422/98; 60/276; 123/489; 204/406; 204/412; 204/425
[58] Field of Search ............. 204/406, 412, 425, 1 S; 60/276; 123/489; 324/425; 422/88, 98

[56] References Cited

U.S. PATENT DOCUMENTS 4,578,171 3/1986 Yamada et al. .............. 204/410
4,594,139 6/1986 Asayama et al. ............. 204/425
4,601,809 7/1986 Kitahara ..................... 204/425

FOREIGN PATENT DOCUMENTS 2083629 3/1982 United Kingdom ............. 204/406

Primary Examiner—David L. Lacey
Assistant Examiner—Floyd Bennett
Attorney, Agent, or Firm—Birch, Stewart, Kolasch & Birch

[57] ABSTRACT

An oxygen concentration sensing device for sensing an oxygen concentration in a gaseous body includes a pair of solid electrolyte members having oxygen ion permeability which are arranged to face each other forming a predetermined gap portion between them. Each of the solid electrolyte members is provided with a pair of electrodes and one of the solid electrolyte members is operative as an oxygen pump element when a drive current is supplied across the electrodes thereof and the other one of the solid electrolyte members is operative as a sensor cell element for producing a sensor output signal. The sensing device is provided with a current supply circuit for supplying the drive current of the oxygen pump element and a delay control circuit for delaying the increase of the magnitude of drive current of the oxygen pump element at a start time, so as to prevent an overcurrent to the oxygen pump element which otherwise is generated by the current supply circuit and causes the so called blackening phenomenon of the solid electrolyte members.

6 Claims, 9 Drawing Figures

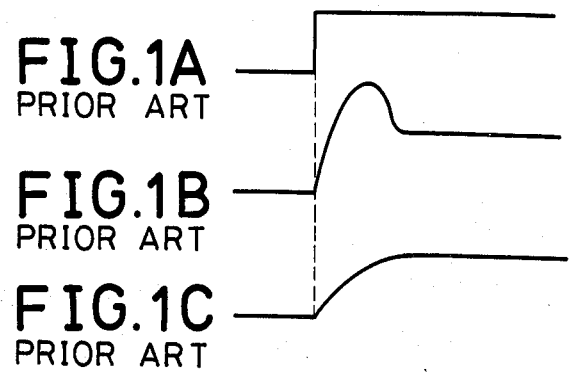
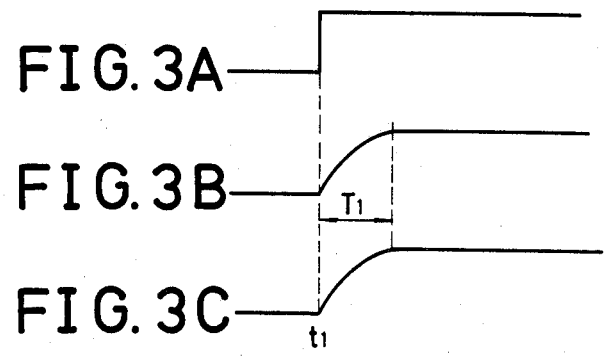

DEVICE FOR SENSING AN OXYGEN CONCENTRATION IN GASEOUS BODY WITH A SOURCE OF PUMP CURRENT FOR AN OXYGEN PUMP ELEMENT

BACKGROUND OF THE INVENTION

1. Field of the Invention

The present invention relates to a device for sensing an oxygen concentration in gaseous body, such as exhaust gas of an internal combustion engine.

2. Description of Background Information

Air-fuel ratio feedback control systems for an internal combustion engine are becoming generally used. They are constructed such that the oxygen concentration in the exhaust gas of the engine is detected by an oxygen concentration sensor and an air-fuel ratio of mixture to be supplied to the engine is feedback controlled in response to a result of the detection of the oxygen concentration so as to purify the exhaust gas and improve the fuel economy.

As an example of an oxygen concentration sensing device for use in the air-fuel ratio control system of the above mentioned type, an oxygen concentration sensing device having an output signal whose level is proportional to the oxygen concentration in test gas (whose oxygen concentration is to be measured) is described in Japanese Patent Application laid open No. 58-153155. This oxygen concentration sensing device has a sensor element which has a general construction including a pair of flat solid electrolyte members having oxygen ion permeability. These oxygen-ion conductive solid electrolyte members, operative as active plates, are placed in the atmosphere of the oxygen-containing test gas. Further, two electrodes are provided on the front and back surfaces of both of the solid electrolyte members. In other words, each pair of electrodes sandwiches each solid electrolyte member. These two solid electrolyte members each having a pair of eletrodes are arranged in face to face relation with each other to form a gap portion, or in other words, a restricted region between them.

With this arrangement, one of the solid electrolyte members serves as an oxygen pump element and the other one of the solid electrolyte members serves as a sensor cell element for sensing an oxygen concentration ratio. In the atmosphere of the test gas, a drive current is supplied across the electrodes of the oxygen pump element in such a manner that the electrode facing the gap portion is used as a negative electrode. By the supply of this current, the oxygen component of the gas within the gap portion is ionized on the surface of the negative electrode of the solid electrolyte member operating as the oxygen pump element. The oxygen ions migrate through the inside of the oxygen pump element to the positive electrode, where the oxygen ions are released from the surface of the positive electrode in the form of the oxygen gas.

While this movement of oxygen ions is taking place, an electric potential is generated across the electrodes of the solid electrolyte member operating as the sensor cell element because the oxygen concentration is different for the gas in the gap portion and the gas outside the electrodes of the sensor cell element. This difference of the oxygen concentration is caused by a reduction of the oxygen gas component within the gap portion. Then, if the magnitude of the electric current supplied to the sensor cell element is varied so as to maintain the electric potential across the sensor cell element, the magnitude of the electric current varies substantially linearly in proportion to the oxygen concentration of the test gas at room temperature.

In this type of oxygen concentration sensing device, if an excessive current is supplied to the oxygen pump element, it causes the so called blackening phenomenon by which the oxygen ions are removed from the solid electrolyte members. For instance, when zirconium dioxide ($ZrO_2$) is utilized as the solid electrolyte, the oxygen ions ($O_2$) are taken from the zirconium dioxide ($ZrO_2$) so that zirconium (Zr) is separated out. As a result of this blackening phenomenon, deterioration of the oxygen pump element takes place rapidly, to cause a debasement of an operation of the oxygen concentration sensing device as a whole.

In air/fuel ratio control systems using this type of oxygen concentration sensing device, magnitude of the current to be supplied to the oxygen pump element is set at a level below a critical level of the occurence of the blackening phenomenon in order to prevent the said phenomenon. At the same time, the magnitude of current is determined so that the voltage level of the output signal of the oxygen concentration sensing device becomes equal to a predetermined reference voltage under a condition in which the air/fuel ratio of mixture to be supplied to the engine is equal to a target air/fuel ratio. Therefore, by comparing the output signal level of the oxygen concentration sensing device with the reference voltage, detection is performed as to whether the air/fuel ratio of mixture is on the rich side or the lean side with respect to the target air fuel ratio. If the air/fuel ratio control system is of the type in which the air/fuel ratio is controlled by the supply of secondary air, the secondary air is supplied when the rich air/fuel ratio is detected, and the supply of the secondary air is stopped when the lean air/fuel ratio is detected. In this way, the air/fuel ratio of mixture to be supplied to the engine is controlled toward the target air/fuel ratio.

For supplying the current to the oxygen pump element, an arrangement is generally used in which the magnitude of current flowing through the oxygen pump element, i.e. the pump current, is detected and the supply of the pump current is controlled by a constant current circuit which operates according to a result of comparison between the detected magnitude of the pump current and a reference current value.

FIGS. 1A and 1B show the variation of the control voltage supplied to the constant current circuit and the corresponding variation of the current supplied to the oxygen pump element in a conventional arrangement. As shown in FIG. 1A, when the supply of the control voltage to the constant current circuit is initiated, for instance, at the time of the start of the engine, the constant current circuit starts to supply the pump current to the oxygen pump element. However, due to a delay of response of the air/fuel ratio control system, the pump current does not reach a desired constant level immediately. Instead, as shown in FIG. 1B, an overshoot of the pump current occurs during a transitional period. Therefore, a problem has been experienced that the magnitude of the pump current exceeds the critical level of the occurence of the blackening phenomenon so that the blackening phenomenon actually takes place.

In addition, because of the presence of the gap portion between the oxygen pump element and the sensor cell element, a delay in the response of the sensor cell element inevitably arises. Particularly, the level of the output signal does not increase and reach the reference voltage immediately, even though the pump current to the oxygen pump element has risen above the constant current value corresponding to the reference current value after the start of the supply of the pump current. Instead, the output signal level increases gradually as illustrated in FIG. 1C.

For this reason, although the output signal level of the sensor cell element is monitored for detecting an overcurrent flowing through the oxygen pump element in some systems, it has been difficult to prevent the generation of an overcurrent immediately after the start of the supply of the pump current to the oxygen pump element.

OBJECT AND SUMMARY OF THE INVENTION

An object of the present invention is therefore to provide an oxygen concentration sensing device by which the blackening phenomenon is prevented even immediately after the start of the supply of the pump current.

According to the present invention, the oxygen concentration sensing device is provided, in the current supply means, with a delay means such as an integration circuit for gradually increasing the magnitude of the current to the oxygen pump element.

BRIEF EXPLANATION OF THE DRAWINGS

In the drawings, like reference numerals denote like parts, and:

FIGS. 1A through 1C are waveform diagrams showing the operation of a conventional oxygen concentration sensing device;

FIGS. 3A through 3C are waveform diagrams similar to FIGS. 1A through 1C, showing the operation of the oxygen concentration sensing device illustrated in FIG. 2;

DETAILED DESCRIPTION OF THE PREFERRED EMBODIMENTS

Figure 2:
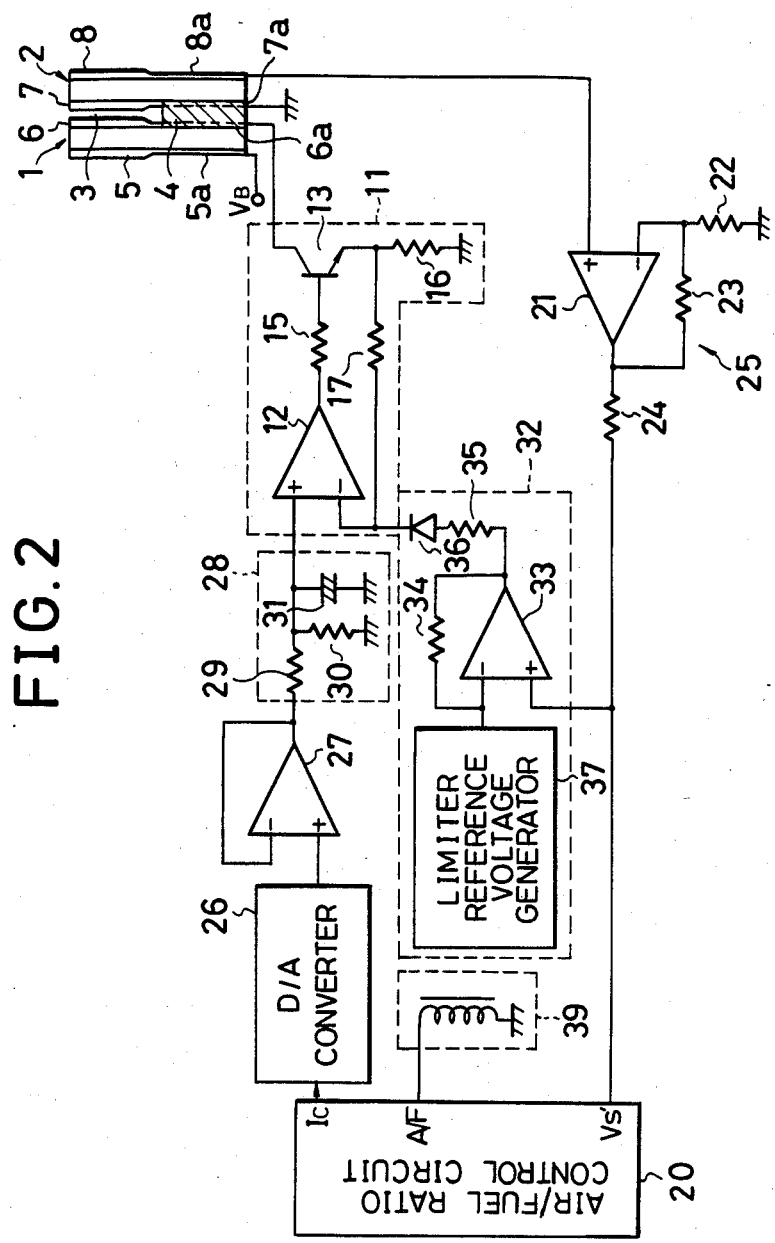
FIG. 2 is a block diagram showing an embodiment of the oxygen concentration sensing device according to the present invention.

FIG. 2 shows an example of an air/fuel ratio control system in which the oxygen concentration sensing device according to the present invention is utilized. In this system, a pair of elements, namely an oxygen pump element 1 and a sensor cell element 2, are arranged parallel to one another. The main portion of the oxygen pump element 1 and the sensor cell element 2, i.e. first and second active plates, are made of an oxygen-ion conductive solid electrolyte member. An end portion of the oxygen pump element 1 and an end portion of the sensor cell element 2 which face each other are spaced apart so as to form gap portion (or a restricted region) 3 between them. The other end portions of the oxygen pump element 1 and the sensor cell element 2 are connected to each other by means of a spacer 4. The oxygen pump element 1 and the sensor cell element 2 are provided, at their free end portions and on both sides thereof, with square electrodes 5 through 8 which are made of porous heat-proof metal. Further, lead wires 5a through 8a of the square electrodes 5 through 8 respectively, are provided on both surfaces of the connected end portions of the oxygen pump element 1 and the sensor cell element 2. The square electrodes 6 and 7 are located in the inner sides of the oxygen pump element 1 and the sensor cell element 2 facing the gap portion 3. Therefore, they are also referred to as inner electrodes. Similarly, the square electrodes 5 and 8 located in the outer sides of the oxygen pump element 1 and the sensor cell element 2 are also referred to as outer electrodes.

Across the electrodes 5 and 6 of the oxygen pump element 1, a constant current is supplied from a constant current source 11. The constant current source 11 is of the attraction type, and is made up of an operational amplifier 12, an NPN transistor 13, and resistors 15 through 17. More particularly, an output terminal of the operational amplifier 12 is connected to the base of the transistor 13 via the resistor 15. The emitter of the transistor 13 is connected to the ground via the resistor 16 and also connected to an inverting input terminal of the operational amplifier 12 via the resistor 17. The collector of the transistor 13 is connected to the inner electrode 6 of the oxygen pump element 1 through the lead wire 6a. The outer electrode 5 of the oxygen pump element 1 is supplied with an electric current having a voltage $V_B$ through the lead wire 5a.

On the other hand, the inner electrode 7 of the sensor cell element 2 is grounded through the lead wire 7a, and the outer electrode 8 of the sensor cell element 2 is connected, through the lead wire 7a, to a noninverting amplifier 25 which is made up of an operational amplifier 21 and resistors 22 through 24. An output terminal of the noninverting amplifier 25 is connected to a $V_{s'}$ input terminal of an air/fuel ratio control circuit 20. An $I_c$ control output terminal of the air/fuel ratio control circuit 20 is connected to a D/A converter 26 which, in turn, generates a voltage corresponding to a digital signal provided at the $I_c$ control output terminal of the air/fuel ratio control circuit 20. The output terminal of the D/A converter 26 is connected to an integrator 28 through a voltage follower circuit 27. The integration circuit 28 is made up of resistors 29 and 30 and a capacitor 31, and whose output signal is supplied to the noninverting input terminal of the operational amplifier 12.

To the output terminal of the noninverting amplifier 25, there is connected a limiter circuit 32. The limiter circuit 32 is made up of an operational amplifier 33, resistors 34 and 35, a diode 36, and a limiter reference voltage generator 37. An inverting input terminal of the operational amplifier 33 is connected to an output terminal of the limiter reference voltage generator 37, and a noninverting input terminal thereof is connected to an output terminal of the noninverting amplifier 25. The operational amplifier 33 supplies a voltage signal whose level corresponds to a difference between the level of an output signal $V_{s'}$ of the noninverting amplifier 25 and a limiter reference voltage $V_L$, to an inverting input terminal of the operational amplifier 12 through the resistor 35 and the diode 36 which is arranged in the forward direction.

The air/fuel ratio control circuit 20 has an A/F drive terminal in addition to the above mentioned $I_c$ control output terminal and $V_{s'}$ input terminal. A solenoid valve 39 for controlling the amount of the secondary air is connected to the A/F drive terminal. The solenoid valve 39 is provided in an air intake side secondary air supply passage which connects to an intake air passage of the engine, at a position downstream from the throttle valve of a carburettor.

With this circuit construction, when a digital signal is supplied from the $I_c$ control terminal of the air/fuel ratio control circuit 20 to the D/A converter 26 at a point of time $t_1$, the digital signal is converted to a control voltage Vc at the D/A converter 26, and in turn supplied to the integration circuit 28 through the voltage follower circuit 27 as illustrated in FIG. 3A. As shown in FIG. 3B, the output signal level of the integration circuit 28 increases gradually due to the presence of the time constant determined by the resistors 29 and 30 and the capacitor 31. In this way, the level of the output signal of the integration circuit 28 reaches a divided voltage of the control voltage Vc by the resistors 29 and 30 after the elapse of a predetermined time period $T_1$ from the point of time $t_1$. The divided voltage thus obtained is in turn supplied to the noninverting input terminal of the operational amplifier 12 as a reference voltage $V_{r1}$.

The pump current $I_p$ following between the electrodes 5 and 6 of the oxygen pump element is detected using a voltage $V_p$ appearing across terminals of the resistor 16. This terminal voltage $V_p$ of the resistor 16 is supplied to the inverting input terminal of the operational amplifier 12 via the resistor 17. When the terminal voltage $V_p$ is lower than the reference voltage $V_{r1}$, the operational amplifer 12 produces a high level output signal which in turn increases the base current of the transistor 13. As a result, the pump current increases. On the other hand, when the terminal voltage $V_p$ is equal to or greater than the reference voltage $V_{r1}$, the output signal level of the operational amplifier 12 turns low, to decrease the base current of the transistor 15. The pump current is decreased under this condition. Since the above two operations are repeated at a high speed, the pump current becomes stable at a constant current level corresponding to the reference voltage $V_{r1}$.

On the other hand, an electric potential $V_s$ appears across the electrodes 7 and 8 of the sensor cell element 2. As shown in FIG. 3C, from the point of time $t_1$, this electric potential $V_s$ gradually goes up as in the case of conventional devices, to approach a predetermined voltage level after the elapse of a predetermined time period $T_1$ from the point of time $t_1$. This electric potential $V_s$ is amplified by the noninverting amplifier 25, and in turn supplied to the $V_s$, input terminal of the air/fuel ratio control circuit 20. In the air/fuel ratio control circuit 20, the level of the output signal of the noninverting amplifier 25 is compared with a reference voltage $V_{r2}$ correspondng to the target air/fuel ratio. The level of the output signal $V_{s'}$ goes up as the air/fuel ratio of the mixture becomes rich. Therefore, if $V_{s'} > V_{r2}$, it is judged that the air/fuel ratio of mixture being supplied to the engine is on the rich side, and the solenoid valve 35 is actuated to open. Thus, the secondary air is supplied to the engine. If, on the other hand, $V_{s'} \leq V_{r2}$, it is judged that the air/fuel ratio of mixture is on the lean side, and the solenoid valve 35 is deactivated to stop the supply of the secondary air to the engine.

If the voltage across the electrodes 7 and 8, that is, the voltage $V_{s'}$ of the output signal of the noninverting amplifier 25 goes up and exceeds the limiter reference voltage $V_L$, a voltage corresponding to a difference between the output signal $V_{s'}$ and the limiter reference voltage $V_L$ which is obtained by the operational amplifier 33 becomes higher than the terminal voltage Vp.

Therefore, from the output terminal of the operational amplifier 33, a current flows through the resistor 35, the diode 36, the resistor 17, and the resistor 16. This current raises the voltage level of the inverting input terminal of the operational amplifier 12 to lower its output signal level. As a result, the base current of the transistor 13 is decreased so that the pump current $I_p$ of the oxygen pump element 1 is decreased.

Since the limiter reference voltage $V_L$ is set at a level slightly higher than the reference voltage $V_{r2}$, if the output signal level $V_{s'}$ of the noninverting amplifier 25 reaches the limiter reference voltage $V_L$, it means that the operation of the sensing device approaches to the region of occurence of the blackening phenomenon. Moreover, if $V_{s'} > V_L$, the level of the output signal of the operational amplifier 33 rises as the air/fuel ratio becomes rich, to decrease the pump current $I_p$. In this way, the blackening phenomenon is prevented.

Figure 4:
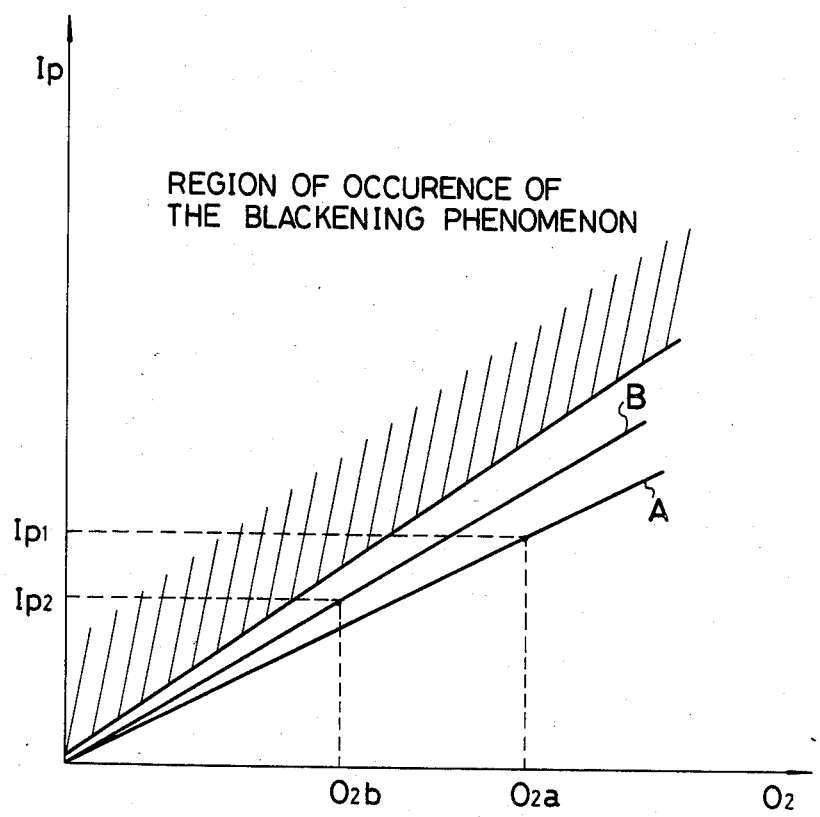
FIG. 4 is a diagram showing a relation between the oxygen concentration in the exhaust gas and the magnitude of the pump current in the device according to the present invention.

FIG. 4 shows a relationship between the pump current and the oxygen concentration $O_2$ in the exhaust gas under a normal air/fuel ratio control operation. In this figure, a value of the oxygen concentration corresponding to a target air/fuel ratio $A/F_a$ is indicated by $O_{2a}$. The reference voltage $V_{r2}$ is set against this value $O_{2a}$ of oxygen concentration, and the magnitude of the pump current $I_p$ is set at a value $I_{p1}$. These values $O_{2a}$ and $I_{p1}$ are expressed by a point on a line A. On the other hand, the upper limit value of the pump current $I_p$ with respect to the oxygen concentration is set such as shown by a line B using the limiter reference voltage $V_L$ as a parameter.

In operation, if the air/fuel ratio of mixture supplied to the engine is changed greatly on the rich side and the detected value of the oxygen concentration is $O_{2b}$, the pump current $I_p$ should be reduced from the value $I_{p1}$ to prevent the blackening phenomenon. If the pump current $I_p$ is maintained at the level $I_{p1}$ under such a condition, the pump current value will enter into an area of occurence of the blackening phenomenon which is shown by oblique lines. However, according to the present invention, the pump current value is reduced to a value $I_{p2}$ under such condition by the operation of the limiter circuit 26.

Figure 5:
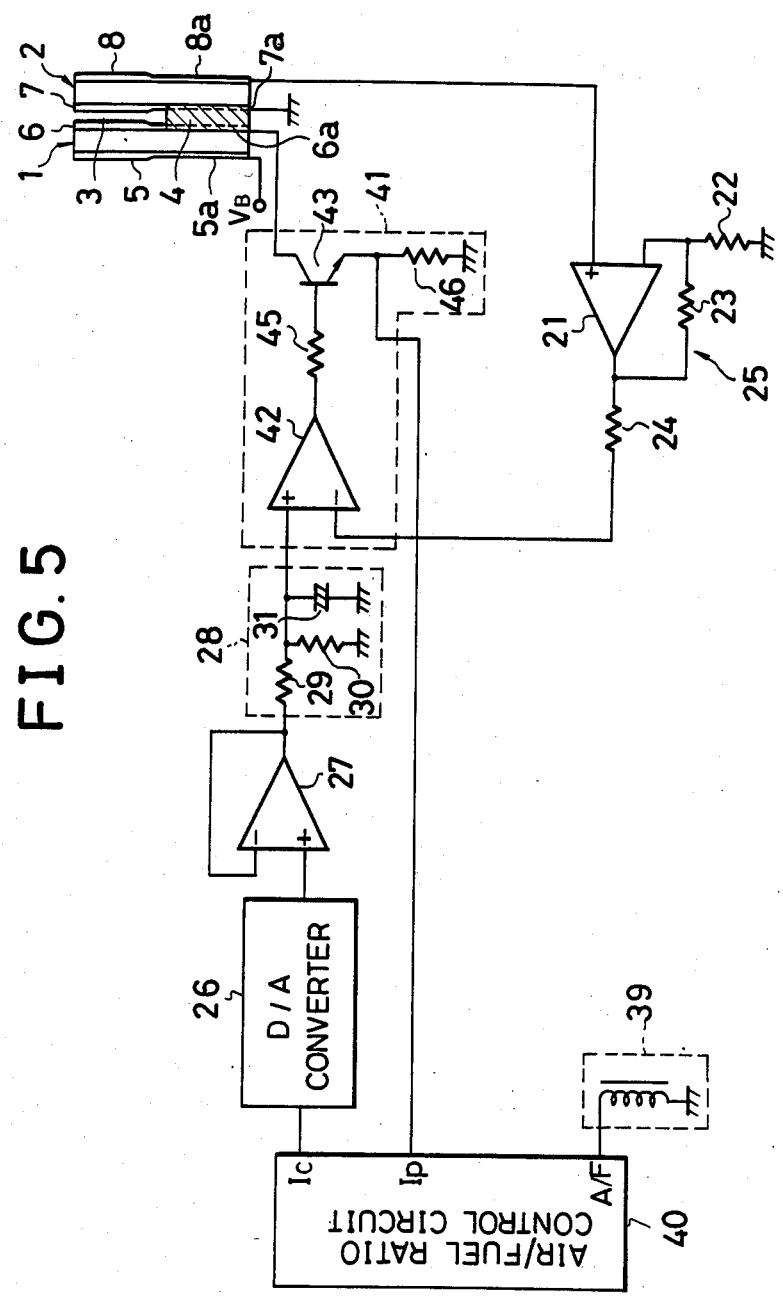
FIG. 5 is a block diagram showing a second embodiment of the oxygen concentration sensing device according to the present invention.

Reference is now made to FIG. 5 in which a second embodiment of the oxygen concentration sensing device according to the present invention is illustrated. In this embodiment of the oxygen conentration sensing device, the digital to analog converter 26, the voltage follower circuit 27 and the integration circuit 28 are provided in the same manner as in the previous embodiment. The output signal of the integration circuit 28 is supplied to a current supply circuit 41 which includes an operational amplifier 42, a transistor 43 and resistors 45 and 46. The output signal of the integration circuit 28 is supplied to a noninverting input terminal of the operational amplifier 42 and an inverting input terminal thereof is supplied with the output signal of the noninverting amplifier 25 which is provided in the same manner as the previous embodiment. With this construction, a current is supplied across the electrodes 5 and 6 of the oxygen pump element 1 from the current supply circuit 41 in accordance with the output signal of the integration circuit 28 so that the voltage $V_s$ developing across the electrodes 7 and 8 of the sensor cell element 2 is maintained constant. The pump current flowing through the oxygen pump element 1 which is detected by means of a terminal voltage Vp of the resistor 46 is supplied to an $I_p$ input terminal of the air/fuel ratio control circuit 40. The air/fuel ratio control circuit 40 detects whether the air/fuel ratio is richer or leaner than the target air/fuel ratio from the voltage $V_p$ applied to its $I_p$ input terminal, and controls the solenoid value 39 in accordance with the detected result.

It will be appreciated from the foregoing, according to the present invention the oxygen concentration sensing device is provided with a delay means for gradually increasing the magnitude of the pump current supplied to the oxgen pump element after the start of the application of the pump current. Thus, the pump current is prevented from entering into the region of the blackening phenomenon irrespective of the delay of the response of the operation of the limiter circuit for preventing the excessive current which might be due to the presence of the gap portion between the oxygen pump element and the sensor cell element.

What is claimed is:

1. An air/fuel ratio control system for controlling an air/fuel ratio of an internal combustion engine in accordance with an oxygen concentration in an exhaust gas of said internal combustion engine, including an oxygen concentration sensing device which comprises:

an oxygen sensing unit being sensitive to oxygen in an oxygen-containing gas and operative to produce an output signal having a magnitude proportional to the concentration of oxygen in the oxygen-containing gas when contacted by a stream of the gas and having a sensor cell element made of a first active plate of an oxygen-ion conductive solid electrolyte and a first pair of electrodes sandwiching said first active plate, an oxygen pump element made of a second active plate of an oxygen-ion conductive solid electrolyte and a second pair of electrodes sandwiching said second active plate, said first and second active plates confronting a restricted region into which said oxygen-containing gas is introduced;

current supply means, connected to said oxygen pump element, for supplying a drive current across the electrodes of said oxygen pump element so that a sensor output signal whose level is proportional to an oxygen concentration of said oxygen-containing gas is generated at said sensor cell element; and delay control means, connected to said current supply, means for gradually increasing said drive current to said oxygen pump element.

2. A system as set forth in claim 1, further comprising a source of a first predetermined control voltage wherein:

said current supply means is a constant current source means having a first control input terminal for receiving the first predetermined control voltage and a second control input terminal for receiving a second control voltage which varies in proportion to a magnitude of said drive current supplied across the electrodes of said oxygen pump element, said constant current source means controlling the magnitude of said drive current in response to a difference between said first and second control voltages, and wherein said delay control means is an integration circuit means connected between said source of said first predetermined control voltage and said first control input terminal of said constant current source means.

3. A system as set forth in claim 2, further comprising a limiter circuit means for producing a limiter voltage signal to be supplied to said second control input terminal of said constant current source means in response to the level of said sensor output signal produced by said sensor cell element.

4. A system as set forth in claim 1, wherein said current supply means is a current source means having a first control input terminal for receiving a first predetermined control voltage and a second control input terminal for receiving a second control voltage which varies in proportion to the level of said sensor output signal generated by said sensor cell element, said current source means controlling the magnitude of said drive current in response to a difference between said first and second control voltages, and wherein said delay control means is an integration circuit means connected between a source of said first predetermined control voltage and said first control input terminal of said current source means.

5. An air/fuel ratio control system for controlling an air/fuel ratio of an internal combustion engine in accordance with an oxygen concentration in an exhaust gas of said internal combustion engine, including an oxygen concentration sensing device which comprises:

an oxygen sensing unit being sensitive to oxygen in an oxygen-containing gas and operative to produce an output signal having a magnitude proportional to the concentration of oxygen in the oxygen-containing gas when contacted by a stream of the gas and having a sensor cell element made of a first active plate of an oxygen-ion conductive solid electrolyte and a first pair of electrodes sandwiching said first active plate, an oxygen pump element made of a second active plate of an oxygen-ion conductive solid electrolyte and a second pair of electrodes sandwiching said second active plate, said first and second active plates confronting a restricted region into which said oxygen-containing gas is introduced;

current supply means, connected to said oxygen pump element and said sensor cell element, for supplying a drive current across the electrodes of said oxygen pump element and controlling a magnitude of said drive current so that a constant output voltage is generated at said sensor cell element, and said magnitude of said drive current represents an oxygen concentration of said oxygen containing gas; and delay control means, connected to said current supply means, for gradually increasing said drive current to said oxygen pump element.

6. A system as set forth in claim 5, further comprising a source of a first predetermined control voltage wherein:

said current supply means is a current source means having a first control input terminal for receiving the first predetermined control voltage and a second control input terminal for receiving a second control voltage representing a magnitude of output voltage generated across the electrodes of said sensor cell element, said current source means controlling the magnitude of said drive current in response to a difference between said first and second control voltages so that said magnitude of output voltage generated across the electrodes of said sensor cell element is maintained constant, and wherein said delay control means is an integration circuit means connected between said source of said first predetermined control voltage and said first control input terminal of said current source means.

* * * * *